United States Patent
Yanai et al.

(10) Patent No.: US 9,127,680 B2
(45) Date of Patent: Sep. 8, 2015

(54) VERIFICATION OF MAGNETIC BALANCE FOR MAGNETICALLY LEVITATED IMPELLER

(71) Applicant: THORATEC CORPORATION, Pleasanton, CA (US)

(72) Inventors: Masamichi Yanai, Ann Arbor, MI (US); Jason C. Nanna, Plymouth, MI (US)

(73) Assignee: Thoratec Corporation, Pleasanton, CA (US)

( * ) Notice: Subject to any disclaimer, the term of this patent is extended or adjusted under 35 U.S.C. 154(b) by 336 days.

(21) Appl. No.: 13/857,441

(22) Filed: Apr. 5, 2013

(65) Prior Publication Data
US 2014/0298905 A1    Oct. 9, 2014

(51) Int. Cl.
*G01M 1/02* (2006.01)
*F04D 15/00* (2006.01)
*A61M 1/10* (2006.01)
*F04D 29/048* (2006.01)

(52) U.S. Cl.
CPC ............ *F04D 15/0088* (2013.01); *A61M 1/101* (2013.01); *F04D 29/048* (2013.01)

(58) Field of Classification Search
CPC ..................... F04D 15/0088; F04D 29/048
USPC .......................... 73/455, 168, 865.3
See application file for complete search history.

(56) References Cited

U.S. PATENT DOCUMENTS

| | | |
|---|---|---|
| 7,470,246 B2 | 12/2008 | Mori et al. |
| 2001/0016170 A1 | 8/2001 | Ozaki et al. |
| 2001/0031210 A1 | 10/2001 | Antaki et al. |
| 2004/0116769 A1 | 6/2004 | Jassawalla et al. |
| 2005/0008496 A1 | 1/2005 | Tsubouchi et al. |
| 2011/0129373 A1 | 6/2011 | Mori |
| 2012/0245680 A1 | 9/2012 | Masuzawa et al. |

OTHER PUBLICATIONS

Korean International Searching Authority, International Search Report and Written Opinion as received in PCT Application PCT/US2014/033178 dated Aug. 14, 2014.

*Primary Examiner* — John Chapman, Jr.
(74) *Attorney, Agent, or Firm* — Kilpatrick Townsend & Stockton LLP

(57) ABSTRACT

The magnetic balance is verified of a magnetically-levitated impeller of a centrifugal pump with a pump housing having levitation magnets. The impeller includes embedded magnets and is movable within a chamber in the pump housing between first and second sides of the chamber. The centrifugal pump is mounted on an acceleration fixture while the impeller is held against a predetermined one of the first and second sides by the levitation magnets. A plurality of predetermined accelerations are applied to the acceleration fixture to exert a plurality of different forces of acceleration on the impeller. A determination is made whether the impeller detaches from the predetermined side as a result of each different force of acceleration to identify adjacent forces for which a transition occurs between detaching and not detaching. The transition is compared with a desired retention force to determine whether the pump achieves magnetic balance.

8 Claims, 5 Drawing Sheets

VERIFICATION OF MAGNETIC BALANCE FOR MAGNETICALLY LEVITATED IMPELLER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices having a centrifugal blood pump with a levitated impeller, and, more specifically, to a testing method to verify whether a manufactured pump provides the proper magnetic forces on the impeller to maintain a balanced, center position of the levitated impeller.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. The impeller acts as a rotor of an electric motor in which a rotating magnetic field from a multiphase stator couples with the impeller and is rotated at a speed appropriate to obtain the desired blood flow through the pump.

The centrifugal pump employs a sealed pumping chamber. By levitating the impeller within the chamber when it rotates, turbulence in the blood is minimized. The spacing between the impeller and chamber walls minimizes pump-induced hemolysis and thrombus formation. The levitation is obtained by the combination of a magnetic bearing and a hydrodynamic bearing. For the magnetic bearing, the impeller typically employs upper and lower plates having permanent magnetic materials for interacting with a magnetic field applied via the chamber walls. For example, a stationary magnetic field may be applied from the upper side of the pump housing to attract the upper plate while a rotating magnetic field from the lower side of the pump housing (to drive the impeller rotation) attracts the lower plate. The hydrodynamic bearing results from the action of the fluid between the impeller and the chamber walls while pumping occurs. Grooves may be placed in the chamber walls to enhance the hydrodynamic bearing (as shown in U.S. Pat. No. 7,470,246, issued Dec. 30, 2008, titled "Centrifugal Blood Pump Apparatus," which is incorporated herein by reference). The magnetic and hydrodynamic forces cooperate so that the impeller rotates at a levitated position within the pumping chamber.

A particular pump design will specify the strength and placement of all the interacting magnets in such a way that the impeller receives a desired balancing force when it is at the centered (i.e., levitated) position. Each magnet and the various plastic parts can be tested for compliance with their design specifications in an attempt to make sure that the pump will perform as intended. During assembly, however, small variations both from assembly tolerances and from aggregate small errors in the components can appear which impair the magnetic balance.

The magnetic balance is not intended to be perfect. Impeller rotation in the presence of a pumped fluid (e.g. blood) is necessary so that the hydrodynamic and magnetic forces can cooperate to achieve the balanced position. When the pump is empty and the impeller is not rotating, the lack of hydrodynamic force means that the impeller is not suspended but is magnetically held against one of the sides of the chamber. Thus, visual inspection cannot reveal whether a satisfactory magnetic balance is present. It would be desirable to verify proper force balancing without requiring pump operation with a fluid.

SUMMARY OF THE INVENTION

In one aspect of the invention, a method is provided for verifying magnetic balance of a magnetically-levitated impeller of a centrifugal pump. The pump includes a pump housing having levitation magnets for providing a levitation field. The impeller includes embedded magnets. The pump housing defines a chamber containing the impeller, and the impeller is axially movable between first and second sides of the chamber. The centrifugal pump is mounted on an acceleration fixture while the impeller is held against a predetermined one of the first and second sides by the levitation magnets. A desired retention force is determined for holding the impeller against the predetermined side that corresponds to a desired balance force to be applied to the impeller when levitated away from the predetermined side. A first predetermined acceleration is applied to the acceleration fixture that corresponds to a force of acceleration on the impeller less than the desired retention force. It is determined whether the impeller detached from the predetermined side, and an unbalanced condition is detected if the impeller has detached. With the impeller held against the predetermined side, a second predetermined acceleration is applied to the acceleration fixture that corresponds to a force of acceleration on the impeller greater than the desired retention force. It is determined whether the impeller detached from the predetermined side, and an unbalanced condition is detected if the impeller did not detach.

DETAILED DESCRIPTION OF PREFERRED EMBODIMENTS

Figure 1:
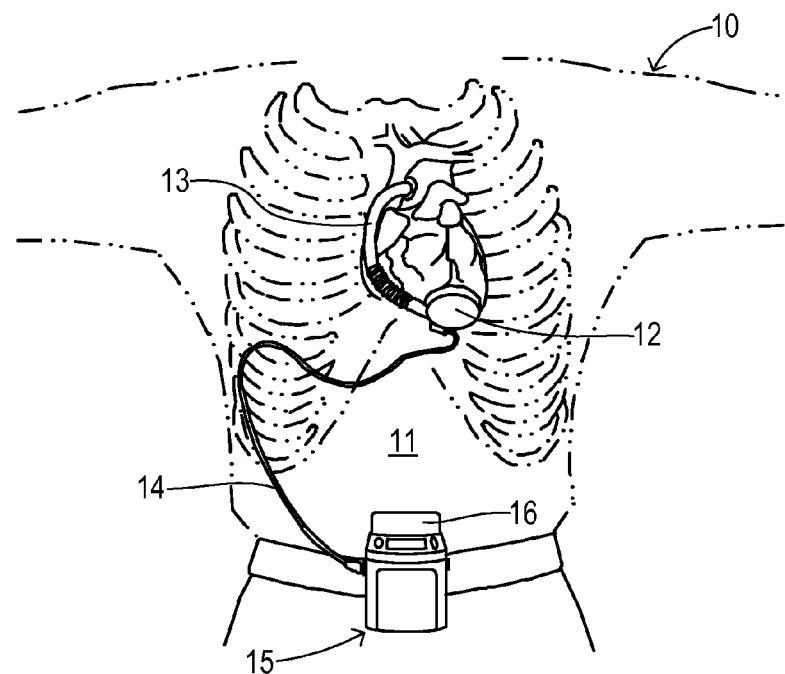
FIG. 1 is a front view of a left ventricular assist system having a pump implanted into a patient.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A percutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery. Control unit 15 includes a commutator circuit for driving a motor stator within pumping unit 12.

Figure 2:
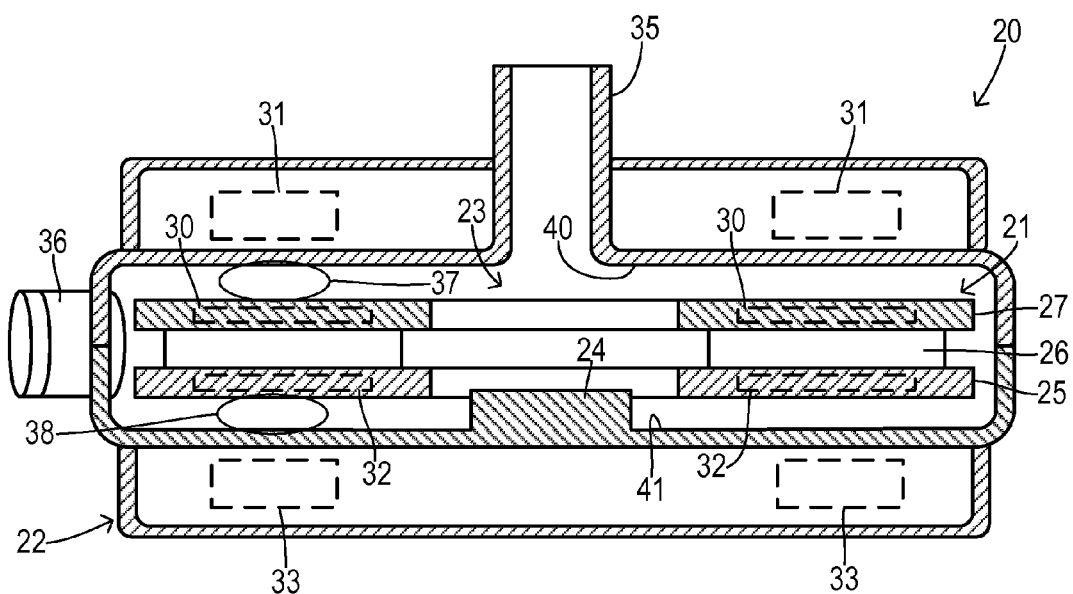
FIG. 2 is a cross section of a centrifugal pump having an impeller levitated by magnetic and hydrodynamic bearing forces.
Figure 3:
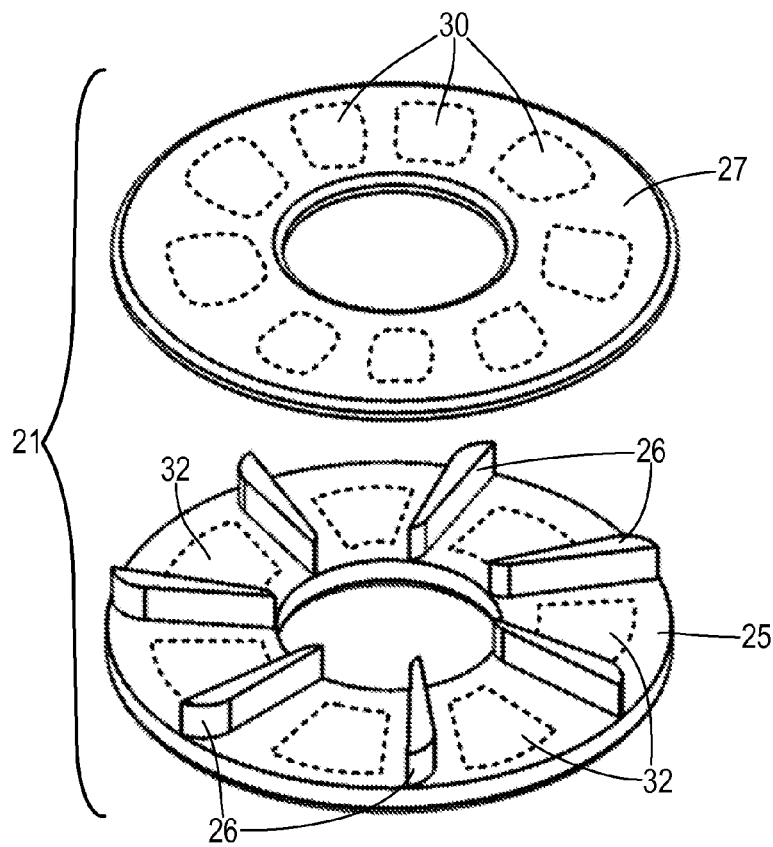
FIG. 3 is an exploded, perspective view of the impeller of FIG. 2.

FIG. 2 shows a centrifugal pump unit 20 having an impeller 21 and a pump housing 22. Impeller 21 is disposed within a pumping chamber 23 over a hub 24. As also shown in FIG. 3, impeller 21 includes a first plate or disc 25 and a second plate or disc 27 sandwiched over a plurality of vanes 26. Second disc 27 includes a plurality of embedded magnet segments 30 for interacting with a levitating magnetic field created by levitation magnet structure 31 disposed in housing 22. Magnet structure 31 preferably is comprised of one or more permanent magnet segments providing a symmetrical, static levitating magnetic field around a 360° circumference. First disc 25 contains embedded magnet segments 32 for magnetically coupling with a magnetic field from stator magnets 33 disposed in housing 22. Stator magnets 33 can be either permanent magnets (e.g., mounted to a rotor) or electromagnetic coils driven by a pulse-width modulated voltage, for example. Housing 22 includes an inlet 35 for receiving blood from a patient's ventricle and distributing it to vanes 26. Impeller 21 is preferably circular and has an outer circumferential edge. By rotatably driving impeller 21, the blood received at an inner edge of impeller 21 is carried to the outer circumferential edge and leaves the pump via an outlet 36. Hydrodynamic forces are generated during pump rotation between impeller 21 and upper and lower walls 40 and 41, respectively of chamber 23, such as in the areas designated 37 and 38. Various features such as grooves (not shown) may be incorporated in walls 40 and 41 to enhance and direct the hydrodynamic forces as is known in the art. Before the pump is filled with fluid or rotation is started, impeller 21 is axially movable between walls 40 and 41. When impeller 21 approaches either one of the walls, it becomes captured against that wall by magnetic attraction of the nearby magnets in the corresponding region of housing 22.

Figure 4:
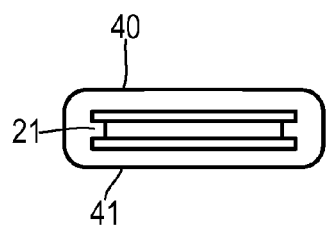
FIGS. 4-6 depict an impeller in a pump chamber at a centered position and at opposite axial sides, respectively.
Figure 5:
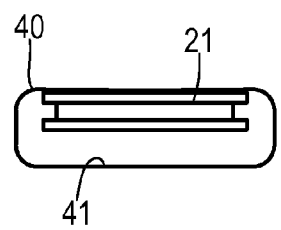
Figure 6:
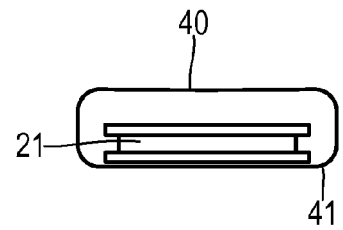

The various axial positions of impeller 21 are shown in FIGS. 4-6. In FIG. 4, impeller 21 is located at a centered position between walls 40 and 41 corresponding to the desired balanced position achieved while the pump is operating. When hydrodynamic forces are absent, impeller 21 is not stable at the centered position. Therefore, it moves axially and is held against either upper wall 40 as shown in FIG. 5 or lower wall 41 as shown in FIG. 6 because the force of magnetic attraction increases as impeller 21 approaches either wall.

Figure 7:
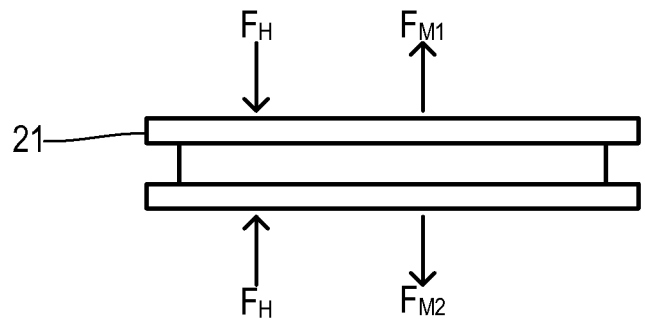
FIG. 7 illustrates the balancing forces that act upon the impeller in the pump chamber.

The forces that act on impeller 21 are summarized in FIG. 7. While pumping a fluid, hydrodynamic forces $F_H$ are generated between impeller 21 and each one of the side walls. The direction of each force $F_H$ is directed toward the center position of impeller 21. As the distance between impeller 21 and a respective sidewall decreases, the associated hydrodynamic force $F_H$ increases. Thus, the hydrodynamic bearing tends to keep impeller 21 at the centered position. In the magnetic bearing, a magnetic force $F_{M1}$ attracts impeller 21 toward top wall 40 and magnetic force $F_{M2}$ attracts impeller 21 toward bottom wall 41. As impeller 21 approaches one wall, the attraction toward that wall increases while the attraction toward the other wall decreases. Consequently, a pump in an inactive state has impeller 21 held against one of the upper or lower walls 40 or 41. The actual holding force which presses impeller 21 against one of the walls is proportional to the magnetic attraction felt by impeller 21 to that side when it is at the centered position. Therefore, the present invention uses a measurement of the holding force at the walls in order to determine whether a magnetic balance is properly obtained when the impeller is located at the centered position. The magnetic force attracting the impeller to one side of the pumping chamber as a result of interaction between one set of magnets in the pump housing is with the respective set of magnets in the upper or bottom plate of the impeller can be estimated as follows:

$$F = \frac{\mu q_1 q_2}{4\pi r^2}$$

where μ is the permeability of the medium (e.g., blood), $q_1$ and $q_2$ are the magnitudes of the magnetic poles, and r is the separation between the magnets.

The desired force to be exerted by each set of magnets in the pump housing on the impeller when at the centered position is specified as part of the pump design. Typically, the desired force from each direction may be specified as a range, such as 0.5 N±10%. The magnetic attraction from each side experienced by the impeller at the center can be used to calculate the holding force it experiences when it is placed against a respective side of the pumping chamber. From the above equation it can be seen that the force is inversely proportional to the square of the separation r between magnets. For example, a desired balance force of 0.5 N±10% might translate to a holding force of 2.0 N±10% (depending upon the specific configuration of the pump).

As a consequence of these relationships, the present invention verifies that the desired magnetic balancing forces are present for a manufactured pump unit by characterizing the holding force(s). In addition to, or instead of, checking that an actual holding force is within a desired absolute range of magnitudes, the invention may check that the magnetic forces being exerted on the impeller from each of the two sides of the pump housing are sufficiently close in magnitude in order to provide magnetic force balancing. For example, the holding force at each side of the pumping chamber is measured and then each measured value is translated into the force that would be exerted with the impeller moved to the centered position. Then the two translated values are compared to verify a net magnetic force that is sufficiently close to zero (i.e., balanced).

Figure 8:
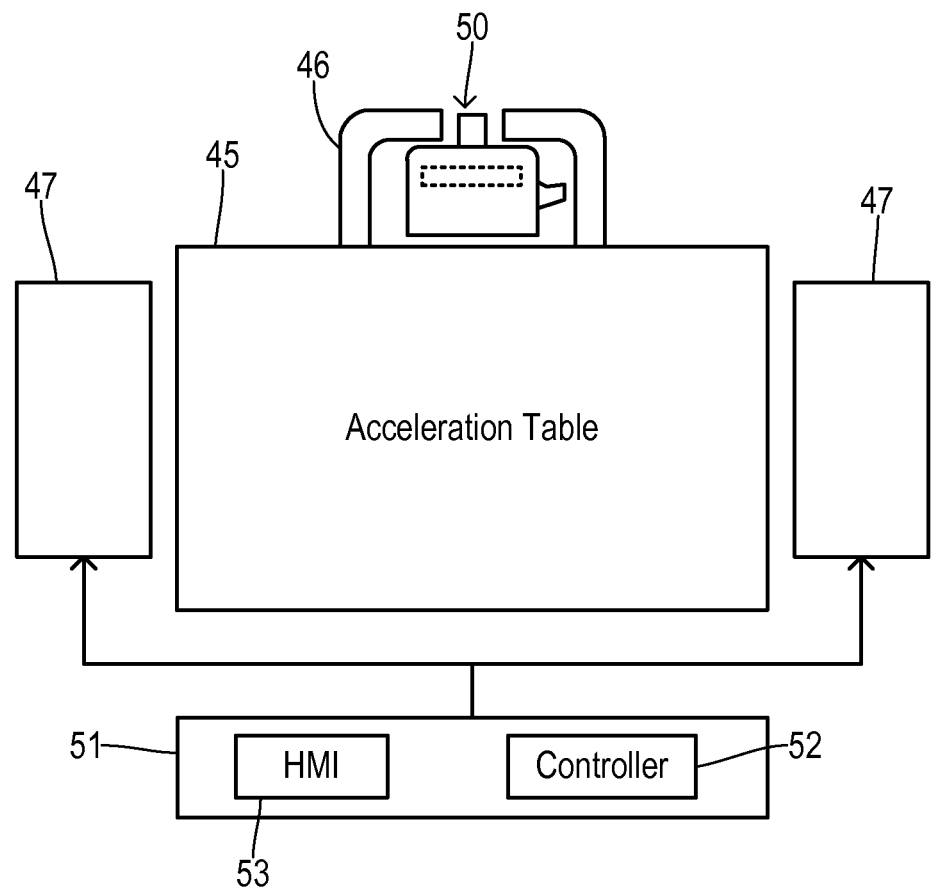
FIG. 8 illustrates a test apparatus for verifying whether a centrifugal pump provides a magnetic balance to the impeller.

A basic setup for the present invention is shown in FIG. 8. An acceleration table includes a main mass 45 having a fixture 46. A pump unit 50 to be tested can be secured to fixture 46. A table driver 47 is disposed adjacent to table mass 45 for generating the desired forces for accelerating mass 45 and fixture 46 so that a controlled acceleration can be applied to pump 50. A controller 51 is connected to drivers 47 and includes a microcontroller/computer 52 and an HMI 53 used by an operator to execute desired operations and to obtain the test results. Although table 45 and fixture 46 are shown in an arrangement for providing vertical acceleration, a horizontal orientation could also be used so that the force of gravity can be ignored. Furthermore, the acceleration table as disclosed herein also includes a centrifuge configuration in which the fixture is rotated at a speed which is controlled to provide the desired acceleration force.

Figure 9:
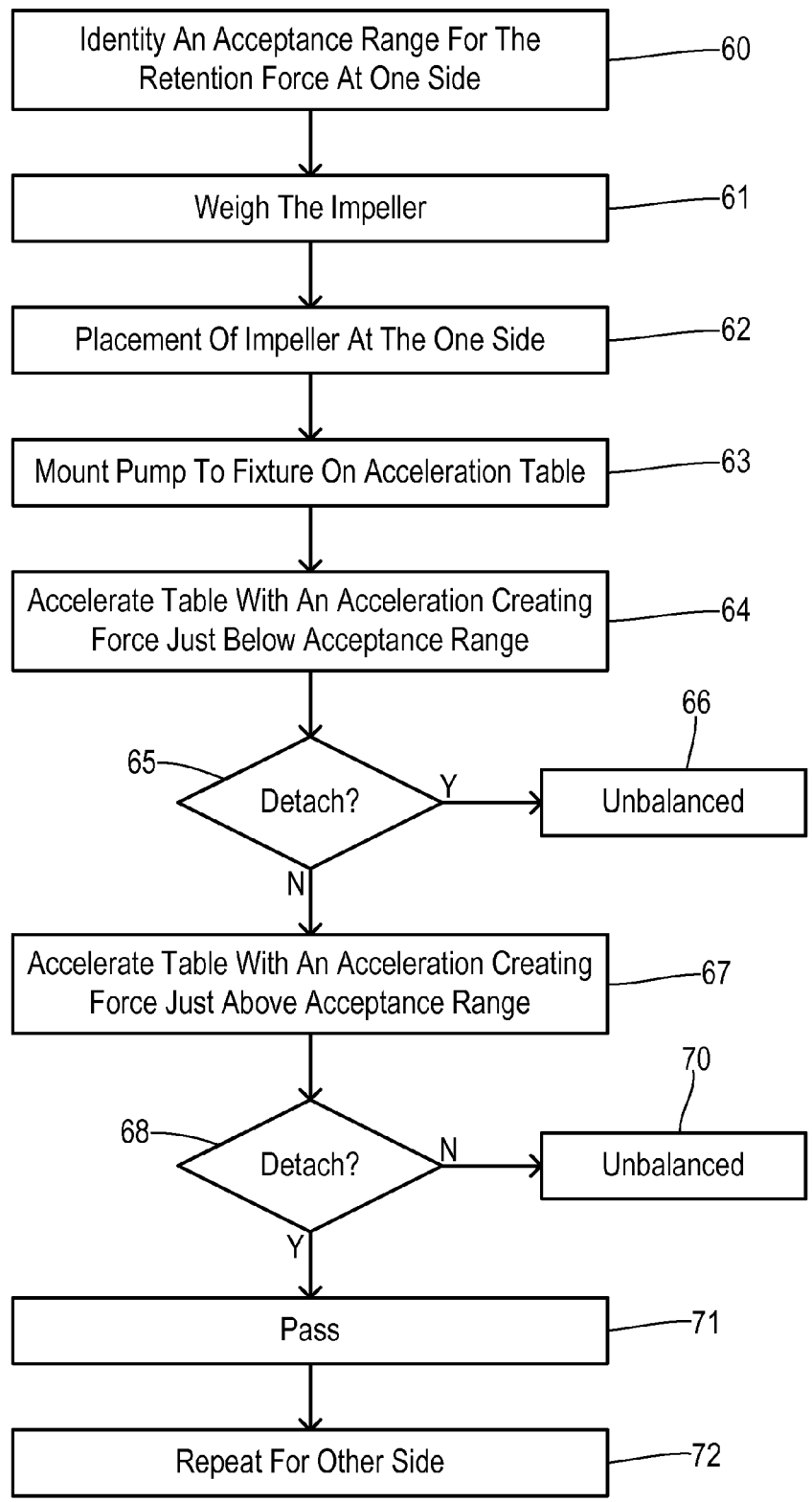
FIG. 9 is a flowchart showing a first embodiment of a method of the present invention.

One preferred method of the invention is shown in FIG. 9. In step 60, an acceptance range for a retention force that holds the impeller at one predetermined side of the pump housing is identified. As describe above, the acceptance range may correspond to a balance force for the center position translated to the corresponding magnetic force exerted when the impeller is located against one axial side of the pumping chamber in the pump housing. The balancing force may be 1) specified according to a pump design or 2) obtained as a result of a previous measurement of a holding force on the opposite side of the pump housing, for example.

In order to accurately apply a known force to the impeller by accelerating the acceleration table, it is important to accurately weigh the impeller in step 61. The force applied to the impeller during an acceleration is equal to the mass times the acceleration. With an accurate weight or mass of the impeller and the ability to accurately control an applied acceleration, a known force can be applied to the impeller to determine whether the actual holding force is within the acceptance range. In other words, the predetermined acceleration to be applied can be determined in response to a value of $F_R/m_{imp}$, where $F_R$ is the retention force and $m_{imp}$ is the mass of the impeller.

In step 62, the impeller is placed at the one predetermined side of the pumping chamber. A typical pump housing for an implantable blood pump is made of transparent plastic, so that a desired impeller placement can be verified by visual is inspection. If the impeller is not at the desired side, it can be accessed through the inlet for pushing the impeller into the desired position on the predetermined side of the chamber.

In step 63, the pump is mounted to the fixture on the acceleration table. The table is accelerated in step 64 with an acceleration chosen to create a force with a magnitude just below the acceptance range and directed opposite to the magnetic force of attraction. If the actual holding force is not less than the acceptance range, then this predetermined acceleration will not overcome the magnetic force of attraction and the impeller will continue to be held against the same side of the pump. A check is made in step 65 to determine whether the impeller detached from the side is a result of the acceleration. If it has, then an unbalanced condition is detected in step 66. The detached condition can be determined by visual inspection to see whether the impeller is still on the same side of the pump housing.

If the impeller did not detach in step 65, then the table is accelerated in step 67 with an acceleration that creates a force just above the acceptance range. A check is made in step 68 to determine whether the impeller detached as a result of this force which is above the acceptance range. If not, then the magnetic attraction is too high and an unbalanced condition is detected in step 70. If the impeller detached, then a passing condition is detected in step 71. If necessary or desired, a similar process can be repeated to verify the magnetic balance force for the other side of the pump housing in step 72.

Figure 10:
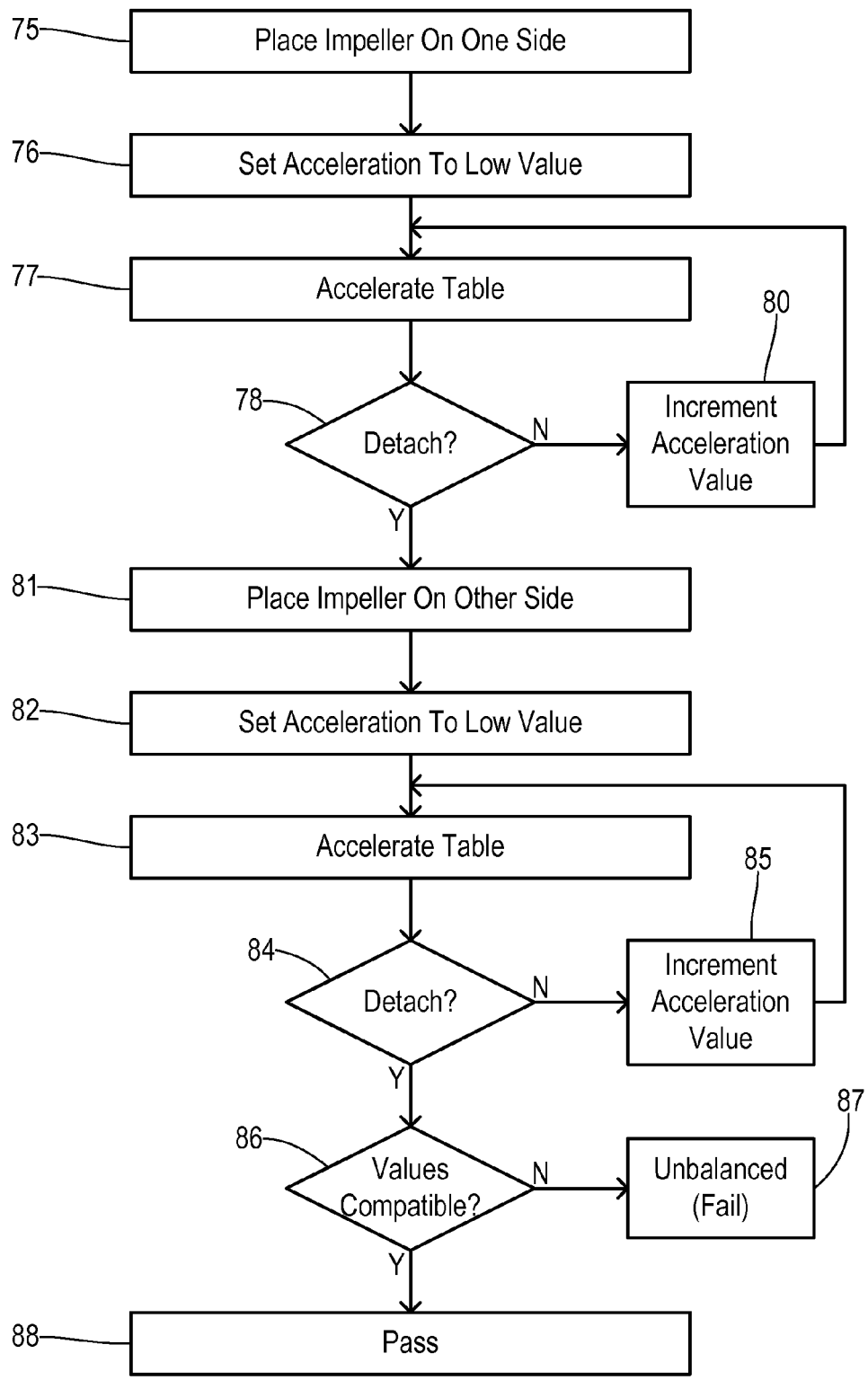
FIG. 10 is a flowchart showing a method according to a second embodiment.

The method shown in FIG. 9 utilizes a minimum number of acceleration trials in order to determine whether the magnetic forces fall within a specified range or not. It may also be desirable to more accurately determine what the actual retention force is. In that case, a method shown in FIG. 10 can be employed. The impeller is placed on one predetermined side of the pump housing in step 75. An acceleration rate for the acceleration table is set to a low value in step 76 to initiate a search for a table acceleration sufficient to detach the impeller. If the value set in step 76 turns out to be high enough to detach the impeller, then the method can be re-started with an even lower value. Based on the set acceleration, the table is accelerated in step 77 and is a check is made in step 78 to determine whether the impeller detached. If not, then the set acceleration value is incremented by a predetermined small step size in step 80. Using the incremented value, the table is again accelerated in step 77 and a check is made in step 78 to determine whether the impeller detached. The acceleration value is stepwise increased until a detachment is detected in step 78. The acceleration value achieving detachment is noted (i.e., stored) and a corresponding magnetic balance force for the centered position can be calculated, if desired.

Having found the holding force for one side of the pump, the impeller can be placed on the other side of the pump housing in step 81 (or the preexisting location of the impeller on that side can be verified). In step 82, the table acceleration is set to a low value. The table is accelerated in step 83 and a check is performed in step 84 to determine whether the impeller detached. If not, the acceleration value is incremented in step 85 for subsequent acceleration of the table in a new trial in step 83. Once the impeller detaches at step 84, the last value for the table acceleration identifies the actual holding force for the other side of the pump housing. In step 86, the two values for the holding forces on opposite sides of the pump housing (or the translated values for the centered position) are checked to determine whether they are compatible. In other words, the net force acting on the impeller when at the center position is checked. If the values are not compatible, then an unbalance condition is detected in step 87. If unbalanced, then the pump unit being tested fails the test and may be discarded. If the values are compatible then the pump unit passes the test in step 88.

The pump unit being tested preferably includes all the components in their final configuration for a single manufactured product. However, testing may sometimes be conducted before final assembly so that the components can be disassembled and some of them replaced for potentially obtaining a pump unit that will pass the test.

What is claimed is:

1. A method of verifying magnetic balance of a magnetically-levitated impeller of a centrifugal pump, wherein the pump includes a pump housing having levitation magnets for providing a levitation field, wherein the impeller includes embedded magnets, wherein the pump housing defines a chamber containing the impeller, and wherein the impeller is axially movable between first and second sides of the chamber, the method comprising the steps of:

mounting the centrifugal pump on an acceleration fixture while the impeller is held against a predetermined one of the first and second sides by the levitation magnets;

determining a desired retention force for holding the impeller against the predetermined side that corresponds to a desired balance force to be applied to the impeller when levitated away from the predetermined side;

applying a first predetermined acceleration to the acceleration fixture that corresponds to a force of acceleration on the impeller less than the retention force;

determining whether the impeller detached from the predetermined side, wherein an unbalanced condition is detected if the impeller has detached;

with the impeller held against the predetermined side, applying a second predetermined acceleration to the acceleration fixture that corresponds to a force of acceleration on the impeller greater than the retention force; and determining whether the impeller detached from the predetermined side, wherein an unbalanced condition is detected if the impeller did not detach.

2. The method of claim 1 wherein the desired retention force is determined as a range, and wherein the first and second predetermined accelerations correspond to forces of acceleration bracketing the range.

3. The method of claim 1 further comprising a repeat of the determining and applying steps with the impeller held against the other one of the first and second sides.

4. The method of claim 1 further comprising the steps of:
weighing the impeller; and
determining the first and second predetermined accelerations in response to a value of $F_R/m_{imp}$, where $F_R$ is the retention force and $m_{imp}$ is the mass of the impeller.

5. The method of claim 4 wherein the first and second predetermined accelerations are applied vertically, and wherein the step of determining the first and second predetermined accelerations is compensated for gravity.

6. A method of verifying magnetic balance of a magnetically-levitated impeller of a centrifugal pump, wherein the pump includes a pump housing having levitation magnets for providing a levitation field, wherein the impeller includes embedded magnets, wherein the pump housing defines a chamber containing the impeller, and wherein the impeller is axially movable between first and second sides of the chamber, the method comprising the steps of:

mounting the centrifugal pump on an acceleration fixture while the impeller is held against a predetermined one of the first and second sides by the levitation magnets;

applying a plurality of predetermined accelerations to the acceleration fixture to exert a plurality of different forces of acceleration on the impeller;

determining whether the impeller detaches from the predetermined side as a result of each different force of acceleration to identify adjacent forces for which a transition occurs between detaching and not detaching;

comparing the transition with a desired retention force to determine whether the pump achieves magnetic balance.

7. The method of claim 6 wherein the desired retention force is proportional to a desired balance force to be applied to the impeller when levitated away from the predetermined side.

8. The method of claim 6 wherein the desired retention force is proportional to a retention force measured with the impeller held against the other one of the first and second sides.

* * * * *